United States Patent
Meyer et al.

(10) Patent No.: US 7,524,310 B2
(45) Date of Patent: *Apr. 28, 2009

(54) APPARATUS FOR APPLYING FLUID IN THE EYE

(75) Inventors: Carsten Helmut Meyer, Marburg (DE); Eduardo Büchele Rodriques, Marburg (DE); Gerrit Jan Vijfvinkel, Geervliet (NL)

(73) Assignee: Dutch Ophthalmic Research Center B.V., Zuidland (NL)

(*) Notice: Subject to any disclaimer, the term of this patent is extended or adjusted under 35 U.S.C. 154(b) by 0 days.

This patent is subject to a terminal disclaimer.

(21) Appl. No.: 11/782,951

(22) Filed: Jul. 25, 2007

(65) Prior Publication Data

US 2008/0027396 A1    Jan. 31, 2008

Related U.S. Application Data

(63) Continuation of application No. 10/881,345, filed on Jun. 30, 2004, now Pat. No. 7,338,477.

(30) Foreign Application Priority Data

Mar. 5, 2004   (NL)   .................................... 1025647

(51) Int. Cl.
    *A61M 35/00*   (2006.01)
(52) U.S. Cl. .................. 604/294; 604/289; 604/290
(58) Field of Classification Search ......... 604/289–290, 604/294; 600/318; 606/4–6, 162
    See application file for complete search history.

(56) References Cited

U.S. PATENT DOCUMENTS

| | | | | |
|---|---|---|---|---|
| 4,602,650 A | * | 7/1986 | Pipkin | 132/317 |
| 4,867,157 A | * | 9/1989 | McGurk-Burleson et al. | 606/170 |
| 4,871,094 A | * | 10/1989 | Gall et al. | 222/386 |
| 4,880,111 A | * | 11/1989 | Bagwell et al. | 206/209.1 |
| 5,066,155 A | * | 11/1991 | English et al. | 401/175 |
| 5,437,274 A | * | 8/1995 | Khoobehi et al. | 600/317 |
| 5,700,146 A | * | 12/1997 | Kucar | 433/82 |
| 5,928,663 A | * | 7/1999 | Peyman | 424/427 |
| 6,241,412 B1 | * | 6/2001 | Spies et al. | 401/129 |
| 6,432,078 B1 | * | 8/2002 | Peyman | 604/27 |
| 6,696,430 B1 | * | 2/2004 | Melles | 514/150 |
| 2003/0171722 A1 | * | 9/2003 | Paques et al. | 604/264 |

FOREIGN PATENT DOCUMENTS

WO   2004/082541 A1   *   9/2004

* cited by examiner

*Primary Examiner*—Michele Kidwell
(74) *Attorney, Agent, or Firm*—Quarles & Brady LLP

(57) ABSTRACT

A surgical hand tool, comprising a handle with a substantially elongated fluid guide extending away therefrom, which fluid guide terminates, at a distal end, in a brush head and is connectable, at a proximal end, to the fluid chamber accommodated in the handle, such that, during use, fluid can flow from the fluid chamber through the fluid guide in order to be dispensed via the brush head, wherein the brush head is accommodated in an insertion sleeve, and is slidable from a first position in which the brush head is located inside the insertion sleeve to a second position in which at least a part of the brush head extends outside the insertion sleeve.

20 Claims, 3 Drawing Sheets

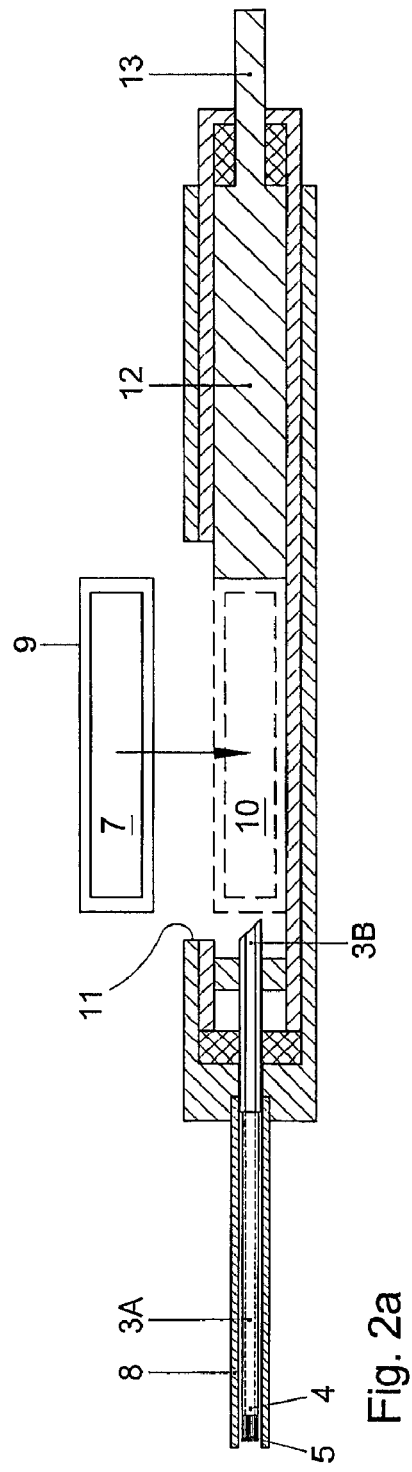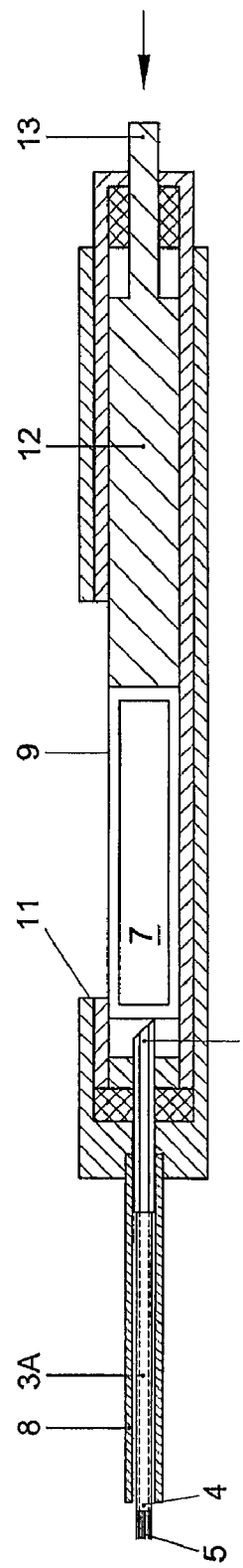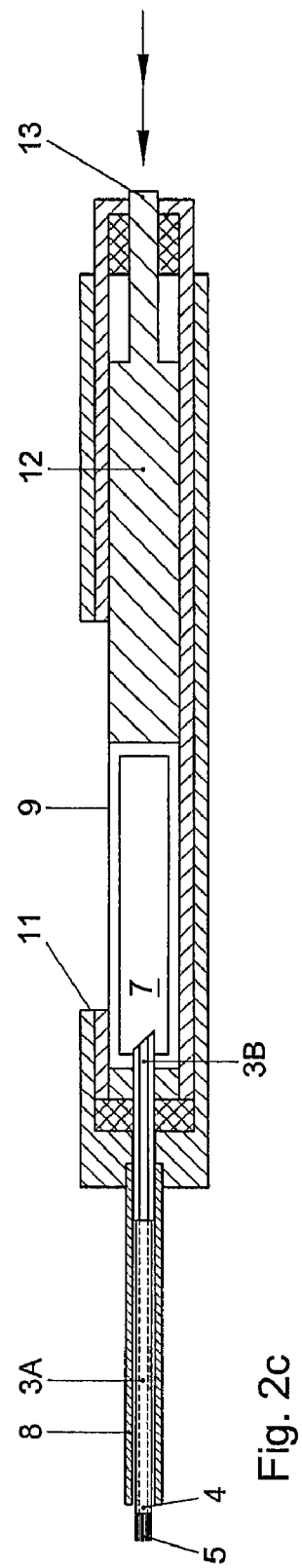
Fig. 2a
Fig. 2b
Fig. 2c

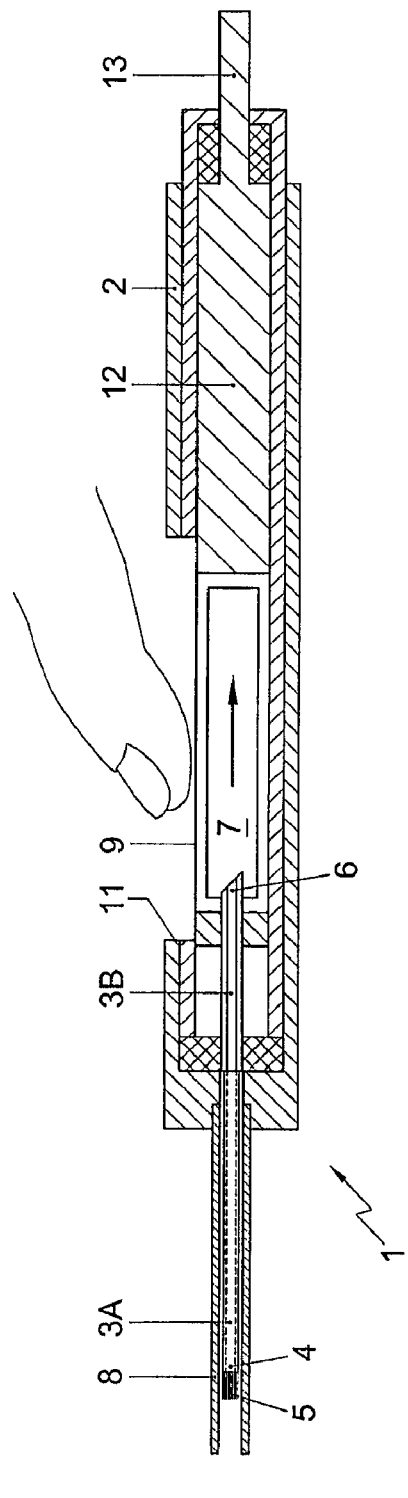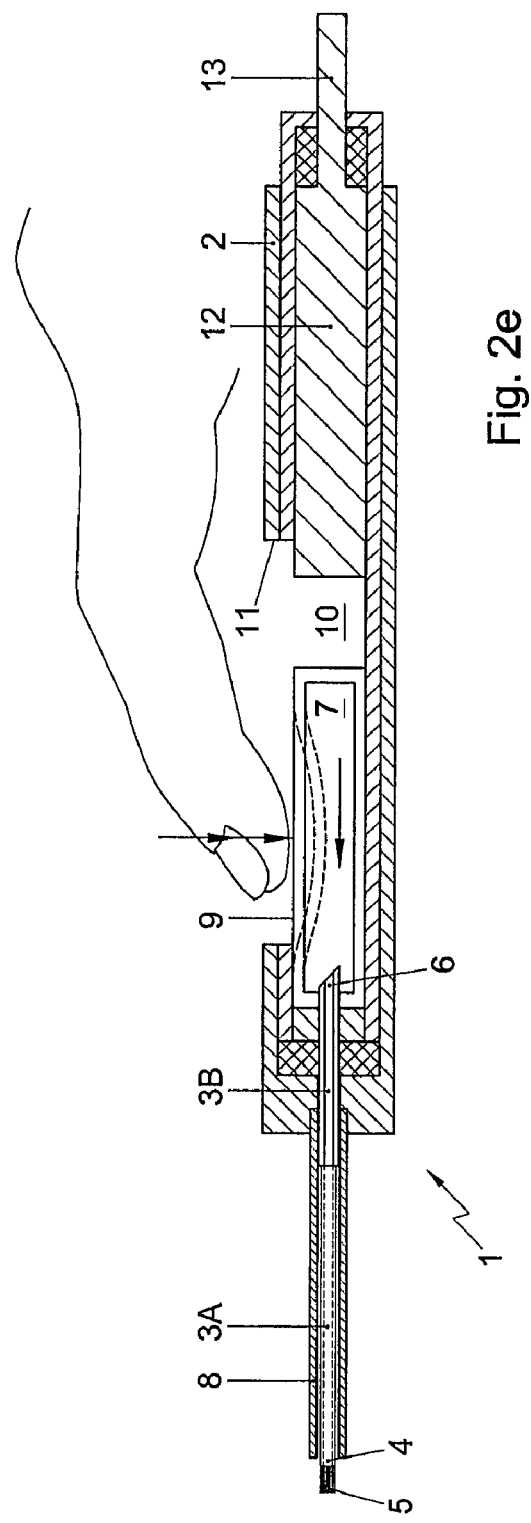

APPARATUS FOR APPLYING FLUID IN THE EYE

CROSS REFERENCES TO RELATED APPLICATIONS

This application is a continuation application of U.S. patent application Ser. No. 10/881,345 filed on Jun. 30, 2004.

STATEMENT REGARDING FEDERALLY SPONSORED RESEARCH

Not Applicable.

The invention relates to an apparatus for applying fluid inside the eye, in particular for applying contrast fluid on the retina of the eye.

During ophthalmic surgery, it may be desired to apply fluid locally in the chamber of the eye, such as a cleaning or rinsing fluid on the retina. Usually, the fluid is applied in drops near the desired location by means of a relatively rigid, hollow tube which, via a small incision, reaches through the wall of the eye into the chamber of the eye. This manner of application involves a number of drawbacks, which, for instance, become strongly manifest when, in ophthalmic surgery, the retina needs to be stained by means of a contrast fluid. For instance, it is difficult to apply the fluid in the proper dose and at the proper location on the retina which is located relatively far at the back of the eye. Further, there is a reasonable chance that the retina is damaged during the application by means of the tube.

The invention contemplates an apparatus for applying fluid in the eye, by means of which above-mentioned drawbacks can be reduced. For this purpose, the invention provides a surgical hand tool, comprising a handle with a substantially elongated fluid guide extending therefrom, which fluid guide terminates, at a distal end, in a brush head and is, at a proximal end, connectable to a fluid chamber accommodated in the handle, such that, during use, fluid can flow from the fluid chamber through the guide in order to be dispensed via the brush head, and in which the brush head is accommodated in an insertion sleeve and is slidable from a first position in which the brush head is located inside the insertion sleeve to a second position in which at least a part of the brush head projects outside the insertion sleeve.

The fluid exiting from the fluid guide can be applied at the desired location in the eye via the brush head and can then be spread by means of the brush head. The soft nature of the brush head allows, even with very delicate eye tissue, such as the retina, direct contact during application between the end of the tool and the tissue, without any damage occurring. By using the brush head which already contacts the tissue during use, further, any thrusts accidentally exerted on the tissue via the tool can be absorbed.

By slidably accommodating the brush head in the protective sleeve, it can be achieved that, in slid in condition, the brush head can easily be passed through a narrow opening in the wall of the eye into the chamber of the eye, while the brush head can then, in slid-out condition, be used for dispensing and spreading the fluid. Preferably, the brush head cannot only be slid out, but also be slid in again. The brush head is then slidable between the first and the second position.

Preferably, the protective sleeve comprises a substantially rigid tube extending outwards from the handle, having a length which is a multiple of the diameter. By means of such a long, narrow tube, the brush head can be properly handled.

Preferably, the fluid guide comprises a flexible tube which is axially slidably accommodated in the tubular protective sleeve. This does not only allow a simple, inexpensive construction of the tool, but further allows the brush head to be carried by the tool in an elegant and slightly resilient manner.

In an elegant manner, the brush head is formed by providing the distal end of the flexible tube with notches extending at least party in axial direction of the tube. The flexible wall segments thus created can then function as brush hairs.

It is noted that it is, of course, well possible to design the brush head in another manner, for instance as a bundle of wires bound together by means of one or more central wires. In such an embodiment, the fluid guide may, for instance, be designed as a rigid, hollow tube through which the central wire extends. Sliding out the brush head can then be carried out by carrying the brush head along with the exiting fluid until the central wire is pulled tight. Any sliding out can be effected by retracting, by means of the central wire, the wire bundle then extending at least partly beyond the distal end of the tube into the fluid guide tube. A good material for such wires are, for instance, sutures from nylon or proline.

Further, the brush head may, for instance, be realized by means of a piece of soft, spongelike material through which and/or along which the fluid can be dispensed.

In an advantageous manner, the fluid chamber is formed by a flexible cartridge in which the fluid to be dispensed is included. Such a flexible cartridge is preferably designed as a separate unit which can be accommodated in the handle and/or can be connected thereto. In an elegant manner, the handle is, for this purpose, provided with a cartridge chamber in which the cartridge can be accommodated. It can thus be achieved that the hand tool can be combined as desired with different types of cartridges in which, each time, different types of fluid are included. The hand tool may, for instance, be supplied with a set of cartridges in which, each time, a different type of contrast fluid is included.

Preferably, such a cartridge comprises a cylindrical wall with compressible sidewalls, preferably from synthetic material, for instance like the ink cartridge for fountain pens known per se. By compression of the wall of the ink cartridge, fluid can then be dispensed via the brush head. The cartridge and the fluid included therein can have been sterilized by means of gamma radiation or in another suitable manner.

In an advantageous manner, the fluid guide is provided, near its proximal end, with a hollow punch by means of which, during use, the fluid chamber, particularly the ink fluid cartridge, can be perforated to realize a fluid connection. Of course, the fluid connection between the fluid chamber and the brush head can be effected during use in many other manners, for instance by removing a flow obstruction or by bringing the fluid chamber into fluid communication with the fluid guide via a screwable connection. An example of this is a fluid cartridge which can be screwed, by a helical movement, onto a punch provided with thread at the distal end of the fluid. Optionally, for instance as an alternative, when the tool is sterilely packaged, the fluid connection may already have been effected at manufacture or assembly of the tool.

In an elegant manner, the hollow punch is slidably bearing-mounted in the cartridge chamber recessed in the handle. When the cartridge in the cartridge chamber in the handle is at least partly accessible to be finger-operated, the brush head can, in that case, be brought from the first position into the second position by sliding with a finger. In such an embodiment, the cartridge is preferably slidably bearing-mounted in the cartridge chamber. Further, with an accessible cartridge, by compressing the sidewall of the cartridge with a finger, fluid can be dispensed. In an advantageous manner, the handle is further provided with a ram slidably accommodated in the cartridge chamber, so that the cartridge can be pressed on the punch in order to effect the fluid connection. In an advantageous manner, an operating rod of the ram reaches from a posterior, distal end of the handle, so that the ram can be thumb-operated.

Further advantageous embodiments of the invention are described in the subclaims.

Within the context of this application, the term brush head is understood to mean a head formed by a soft body by means of which fluid can be applied from the fluid guide onto the eye tissue and can be spread over the tissue without traumatizing the tissue. It is noted that, thus, the brush head is not necessarily provided with elements functioning as brush hairs. But such elements are of course advantageous.

The invention will be further elucidated on the basis of the exemplary embodiment show in a drawing, in which.

Figure 1A:
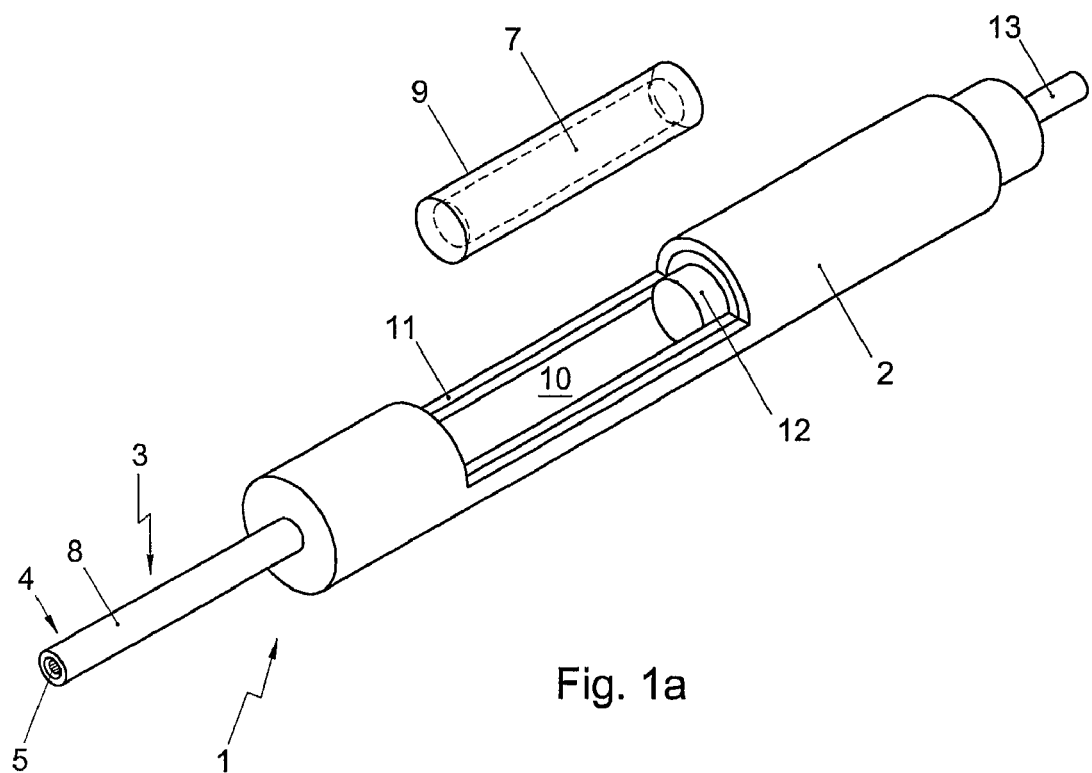
FIG. 1a shows a diagrammatic perspective view of a surgical hand tool with a cartridge chamber which is ready for introducing a fluid cartridge and a brush head located, in a first position, inside the insertion sleeve.

FIG. 2a to FIG. 2e each show a diagrammatic cross section of the surgical hand tool during different stages of operation.

It is noted that the drawings are only a diagrammatic representation of a preferred embodiment of the invention which is given by way of non-limiting exemplary embodiment. In the Figures, the same or corresponding parts are designated by the same reference numerals.

Figure 1B:
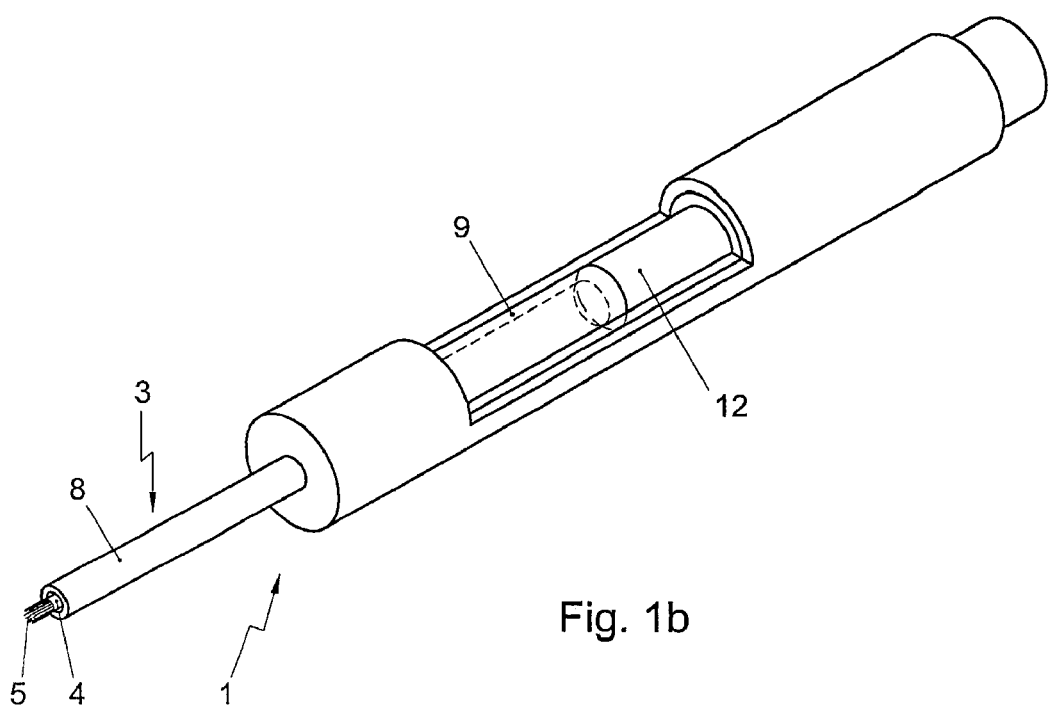
FIG. 1b shows the surgical hand tool of FIG. 1a with the fluid cartridge being accommodated in the fluid chamber and being in fluid connection with the brush head located, in a second position, at least partly freely outside the insertion sleeve.

With reference to FIGS. 1 and 2, shown therein is a surgical hand tool 1, comprising a handle 2 with a substantially elongated fluid guide 3 extending away therefrom. The fluid guide 3 terminates, at a distal end 4, in a brush head 5. The fluid guide 3 is further, at an end proximal with respect to the handle, connectable to the fluid chamber 7 accommodated in the handle 2, such that, during use, fluid can flow from the fluid chamber 7 through the fluid guide 3 in order to be dispensed via the brush head 5. The brush head 5 is accommodated in an insertion sleeve 8. The brush head 5 is slidable from a first position shown in FIG. 1a, in which the brush head 5 is located inside the insertion sleeve 8, to a second position shown in FIG. 1b, in which at least a part of the brush head 5 extends freely outside the insertion sleeve 8.

The insertion sleeve 8 comprises a substantially rigid tube extending from the handle 2, whose length is very much larger than the diameter, for instance in a proportion of 50:1 or more.

In the exemplary embodiment, the fluid guide 3 comprises a flexible tube part 3a which is axially slidably accommodated in the tubular insertion sleeve 8. Here, the flexible tube part is manufactured from silicone material.

The brush head 5 is formed by a number of slits extending in axial direction in the distal end 4 of the flexible tube part 3a, so that the wall parts thus created can behave like hairs of a brush.

The fluid chamber 7 is formed by a flexible cartridge 9 in which the fluid to be dispensed, in this case a contrast fluid for staining the retina, is included. A suitable contrast fluid is, for instance, the fluid which is currently marketed by applicant under the brand name "vision blue". The cartridge and the fluid included therein are sterile.

The cartridge 9 is designed as a separately detachable unit. The handle 2 is provided with a cartridge chamber 10 in which the cartridge 9 can be accommodated. The cartridge is provided with a substantially cylindrical wall from synthetic material, whose sidewalls are compressible.

Here, the fluid guide 3 is provided, at its proximal end, with a hollow punch 3b. In this exemplary embodiment, the hollow punch 3b is slidably bearing-mounted in the cartridge chamber 10 provided in the handle 2.

The handle 2 is provided with a recess 11 in the sidewall, through which the cartridge 9 can be provided in the chamber 10. Further, the sidewall of the cartridge 9 is accessible, when it has been accommodated in the cartridge chamber 10, to be finger-operated via the recess 11.

The cartridge chamber 10 is further provided with a ram 12 for pressing the cartridge 10 on the punch. In this example, the ram 12 is provided with an operating rod 13 reaching outwards from the end of the handle 2 remote from the brush head.

With reference to FIGS. 2a-2e, the operation of the hand tool is as follows. From the initial condition shown in FIG. 2a, the cartridge 9 is provided in the cartridge chamber 10. Then, as shown in FIG. 2b, the operating rod 13 is pressed with the thumb, so that the ram 12 forces the fluid cartridge 9 over the punch 3b. The punch 3b perforates the end wall of the cartridge 9 so that, as shown in FIG. 2c, a fluid connection is created from the fluid chamber 7 surrounded by the cartridge via the fluid guide 3 to the brush head 5.

The cartridge 9 and the fluid guide 3 with the brush head 5 now form one whole. Because of the slidable arrangement of the fluid guide 3 and the punch 3b, the brush head, which had been slid from the first position shown in FIG. 2a to the second position shown in FIG. 2b during the effecting of the fluid connection, can again be brought back into the first position. For this purpose, the index finger is directly contacted with the sidewall of the fluid cartridge 9 via the recess 11 in the sidewall of the handle 2, and the fluid cartridge 9 is drawn back along with the finger, as shown in FIG. 2d. The hand tool is now ready for use.

The distal end of the insertion sleeve 8 can now be introduced, via an incision in the wall of the eye, into the chamber of the eye. Then, as shown in FIG. 2e, with the index finger, the brush head can be slid out from the first position to the second position, after which the brush head can be contacted with the retina. By compressing the sidewall of the cartridge 9 with the finger, the fluid can be dispensed. The dispensing of fluid may be carried out when the brush head contacts the retina, but may, of course, also be carried out when there is (temporarily) no contact between the brush head and retina. In an advantageous manner, brush head and fluid guide are connected to the fluid chamber such that reflux of fluid from the brush head to the fluid chamber is obstructed or is even prevented. This can already be achieved by choosing the flow resistance through the guide and the brush head so as to be large, but may optionally be further strengthened by providing a check valve. It is noted that it may be desired, during preparation for use, after effecting the fluid connection, to already slightly compress the cartridge so that any air can be removed from the fluid guide and the brush head is already moistened.

After sufficient contrast fluid has been applied on the retina, the brush head is brought back from the second position into the first position by sliding back the cartridge with a finger. After this, the tool can be withdrawn from the eye. It is of course also possible to withdraw the tool from the eye while the brush head is in the second position; however, in this embodiment, this is not preferred.

The composition of the contrast fluid may be any composition used in ophthalmology. With advantage, the contrast fluid comprises a vital dye. A suitable vital dye has sufficient dyeing or staining capacity to obtain the desired contrast at concentrations which are physiologically and toxicologically acceptable. Examples of suitable dyes comprise fluorescein, trypan blue, indocyanine green, methylene blue, trypan red, patent blue, brilliant cresyl blue, azophloxine, basic blue (Nile blue sulfate), Bismarck brown, basic red (rhodamine 6G), rose Bengal, eosin, gentian violet, janus green, methylene green, and neutral red. With particular preference, the dye is chosen from fluorescein, indocyanine green, trypan blue, patent blue, gentian violet and methylene blue. It is, of course, also possible to use mixtures of dye.

The contrast fluid is preferably a physiologically compatible solution which is preferably formulated as an aqueous salt solution which is isotonic with eye fluid. The salt in the solution is preferably sodium chloride, sodium phosphate, potassium chloride, calcium chloride, magnesium chloride or a combination thereof. A particularly suitable example is a salt solution, for instance a solution of Ringer with lactic acid added according to Hartmann (Nuijts RMMA, Edelhauser HF, Holley, GP, "Intraocular irrigating solutions: a comparison of Hartmann's lactated Ringer solution, BSS and BSS plus", Clin. Exp. Ophthalmol., vol. 233 (1995), pp. 655-661). According to this embodiment, the salt concentration will be in the range of 0.8 to 1.0 wt. % based on the weight of the solution. It is further recommended that the solution have a neutral pH, that is, a pH between 6.5 and 7.5. An example of a buffer suitable for maintaining this pH for ophthalmic applications is a sodium chloride solution buffered with phosphate.

It is further possible to formulate the contrast fluid as a visco-elastic composition, which may, for instance, be used to protect or even seal intraocular tissue during ophthalmic surgery. Such compositions may be based on inter alia glycosaminoglycans, such as hyaluronic acid, alginic acid, optionally modified collagen, optionally modified cellulose, polyvinyl pyrrolidone, polyvinyl alcohol, polyglucuronic acid, polymannuronic acid and the like and advantageously also contain a vital dye as described hereinabove.

It will be clear that the invention is not limited to the preferred embodiment shown here. Many variations are possible within the scope of the invention as set forth in the following claims.

The invention claimed is:

1. A surgical hand tool, comprising a handle with a substantially elongated fluid guide extending away therefrom, which fluid guide terminates, at a distal end, in a brush head and is connectable, at a proximal end, to a fluid chamber accessed through a recess in the sidewall of the handle, such that, during use, fluid can flow from the fluid chamber through the fluid guide in order to be dispensed via the brush head, wherein the brush head is accommodated in an insertion sleeve, and is slidable from a first position in which the brush head is located inside the insertion sleeve to a second position in which at least a part of the brush head extends beyond the insertion sleeve through an opening in the insertion sleeve.

2. A surgical hand tool according to claim 1, wherein the insertion sleeve comprises a substantially rigid tube extending from the handle.

3. A surgical hand tool according to claim 2, wherein the fluid guide comprises a flexible tube part which is axially slidably accommodated in the tubular insertion sleeve.

4. A surgical hand tool according to claim 3, wherein the brush head comprises a number of slits at least partly extending in axial direction in the distal end of the flexible tube part.

5. A surgical hand tool according to claim 3, wherein the flexible tube part is manufactured from silicone material.

6. A surgical hand tool according to claim 1, wherein the fluid chamber is formed by a flexible cartridge in which the fluid to be dispensed is included.

7. A surgical hand tool according to claim 6, wherein the cartridge is designed as a separately detachable unit.

8. A surgical hand tool according to claim 7, wherein the handle is provided with a cartridge chamber in which the cartridge can be accommodated.

9. A surgical hand tool according to claim 7, wherein the cartridge is provided with a substantially cylindrical wall whose sidewalls are compressible.

10. A surgical hand tool according to claim 1, wherein the fluid chamber is provided with a contrast fluid.

11. A surgical hand tool according to claim 8, wherein the fluid guide is provided, at its proximal end, with a hollow punch in order to make, during use, a fluid connection with the cartridge.

12. A surgical hand tool according to claim 11, wherein the hollow punch is slidably bearing-mounted in the cartridge chamber provided in the handle.

13. A surgical hand tool according to claim 8, wherein, during use, the cartridge provided in the cartridge chamber is accessible to be finger-operated.

14. A surgical hand tool according to claims 11, wherein the cartridge chamber is provided with a ram for pressing the cartridge on the punch.

15. A surgical hand tool according to claim 14, wherein the ram is provided with an operating rod reaching outwards with respect to the handle.

16. A surgical hand tool comprising:
a handle having a sidewall with a recess;
a fluid chamber in said handle and accessed through said recess in said sidewall;
a substantially elongated fluid guide extending away from said handle, said fluid guide having a proximal end and a distal end, said distal end terminating in a brush head, and said proximal end connecting to said fluid chamber; and
an insertion sleeve extending from said handle and slidably receiving said brush head, wherein during use, fluid can flow from the fluid chamber through the fluid guide in order to be dispensed via the brush head, wherein the brush head is slidable from a first position in which the brush head is located inside the insertion sleeve to a second position in which at least a part of the brush head extends beyond the insertion sleeve through an opening in the insertion sleeve.

17. A surgical hand tool according to claim 16, wherein said fluid chamber is formed by a flexible cartridge in which the fluid to be dispensed is included.

18. A surgical hand tool according to claim 17, wherein the cartridge is designed as a separately detachable unit.

19. A surgical hand tool according to claim 16, wherein the cartridge is received in a cartridge chamber formed in said handle.

20. A surgical hand tool according to claim 19, wherein the cartridge is provided with a compressible sidewall accessible through said recess.

* * * * *